United States Patent [19]

Theeuwes et al.

[11] Patent Number: 4,511,352

[45] Date of Patent: Apr. 16, 1985

[54] PARENTERAL DELIVERY SYSTEM WITH IN-LINE CONTAINER

[75] Inventors: Felix Theeuwes, Los Altos; John Urquhart, Palo Alto, both of Calif.

[73] Assignee: ALZA Corporation, Palo Alto, Calif.

[21] Appl. No.: 609,894

[22] Filed: May 14, 1984

[51] Int. Cl.³ .............................................. A11M 5/14
[52] U.S. Cl. ....................................... 604/56; 604/85; 604/92; 604/246
[58] Field of Search .............................. 604/56, 80–85, 604/890–892, 410, 416, 92; 222/95

[56] References Cited

U.S. PATENT DOCUMENTS

| | | |
|---|---|---|
| 2,954,028 | 9/1960 | Smith . |
| 3,001,525 | 9/1961 | Hendricks . |
| 3,305,446 | 2/1967 | Bechtol et al. .......................... 167/72 |
| 3,322,114 | 5/1967 | Portnoy et al. . |
| 3,756,237 | 9/1973 | Chittenden et al. . |
| 3,756,390 | 9/1973 | Abbey et al. ....................... 206/47 A |
| 3,760,984 | 9/1973 | Theeuwes ............................. 222/95 |
| 3,797,485 | 3/1974 | Urquhart . |
| 3,797,494 | 3/1974 | Zaffaroni . |
| 3,845,770 | 11/1974 | Theeuwes et al. . |
| 3,848,603 | 11/1974 | Throner . |
| 3,854,480 | 12/1974 | Zaffaroni . |
| 3,921,635 | 11/1975 | Gauthier . |
| 3,921,636 | 11/1975 | Zaffaroni . |
| 3,941,126 | 3/1976 | Dietrick et al. . |
| 3,948,254 | 4/1976 | Zaffaroni . |
| 3,976,068 | 8/1976 | Lindquist . |
| 3,993,072 | 11/1976 | Zaffaroni . |
| 3,993,073 | 11/1976 | Zaffaroni . |
| 3,995,631 | 12/1976 | Higuchi et al. . |
| 4,061,141 | 12/1977 | Hydes . |
| 4,177,256 | 12/1979 | Michaels et al. ...................... 424/22 |
| 4,203,439 | 5/1980 | Theeuwes . |
| 4,217,894 | 8/1980 | Franetzki . |
| 4,233,973 | 11/1980 | Shulka . |
| 4,256,104 | 3/1981 | Muetterties et al. . |
| 4,323,457 | 4/1982 | Sun et al. ............................ 210/645 |

FOREIGN PATENT DOCUMENTS 497181  9/1969  Switzerland .
982107  9/1963  United Kingdom .

OTHER PUBLICATIONS

Paxinos, J. and Samuels, T. M.; Am. J. Hosp. Pharm., vol. 32, pp. 892–897, Sep. 1975.
Goodwin, H. N., The American Journal of I. V. Therapy, pp. 27–30, Dec.–Jan. 1975.
Masson, A. H. B., Brit. J. Anaesth., vol. 43, pp. 681–686, (1971).
Ferenchak et al., Surgery, vol. 70, No. 5, pp. 674–677, Nov., 1971.

Primary Examiner—Stephen C. Pellegrino
Attorney, Agent, or Firm—Paul L. Sabatine; Edward L. Mandell; Steven F. Stone

[57] ABSTRACT

A parenteral delivery system is disclosed for delivering a beneficial agent to an agent recipient. The delivery system comprises a reservoir, a drip chamber and a flexible container that collapses as agent formulation leaves the system.

12 Claims, 16 Drawing Figures

FIG. 15
FIG. 16
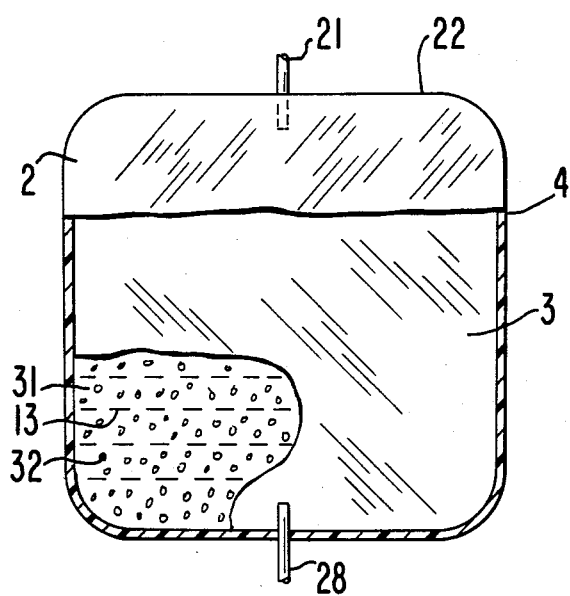
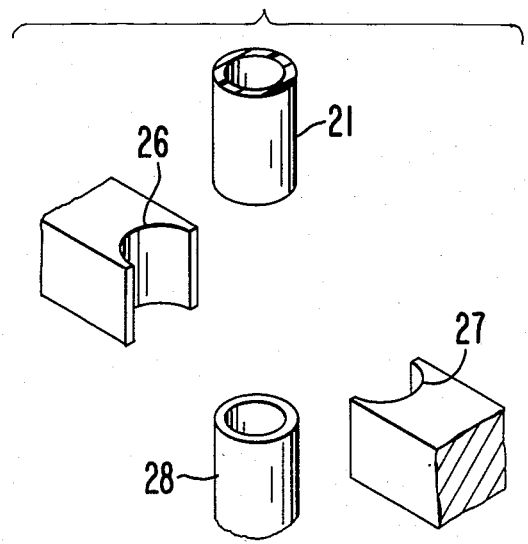

PARENTERAL DELIVERY SYSTEM WITH IN-LINE CONTAINER

FIELD OF THE INVENTION

This invention pertains to a parenteral delivery system. The delivery system comprises a reservoir containing a parenterally administrable fluid, a drip chamber, and an in-line collapsible container containing a parenterally administrable beneficial agent.

BACKGROUND OF THE INVENTION

The parenteral administration of beneficial agents is an established clinical practice. Presently, the beneficial agent is administered by using a parenteral delivery system. The parenteral system contains the beneficial agent in a premixed formulation comprising a parenterally administrable fluid, suspended above a beneficial agent recipient. While this form of parenterally administration is widely used and leads to successful therapy, there is still a great deal of dissatisfaction with the type of parenteral delivery system. For example, the system now used for this purpose must be stored as lower temperatures, often in the frozen state to prevent degradation of the beneficial agent. Additionally, they are bulky and require extensive areas for their use.

DESCRIPTION OF THE INVENTION

In view of the above presentation, it is immediately apparent a need exists for a parenteral delivery system comprising a formulation chamber that overcomes the dissatisfaction associated with the prior art. The invention of this application provides a practical and useful solution to the above problem. This invention makes available a parenteral delivery system comprising a formulation container that can be used clinically for administering a beneficial agent according to a preselected therapeutic program essentially-free from the dissatisfactions of the prior art.

BRIEF DESCRIPTION OF THE DRAWING FIGURES

FIG. 15 is a back view in opened section of the formulation container depicting its structure and a parenterally administrable fluid and a beneficial agent in the container; and, FIG. 16 is a fragmented view depicting the portions of the formulation container designed for receiving an incoming and outgoing tube.

Figure 1:
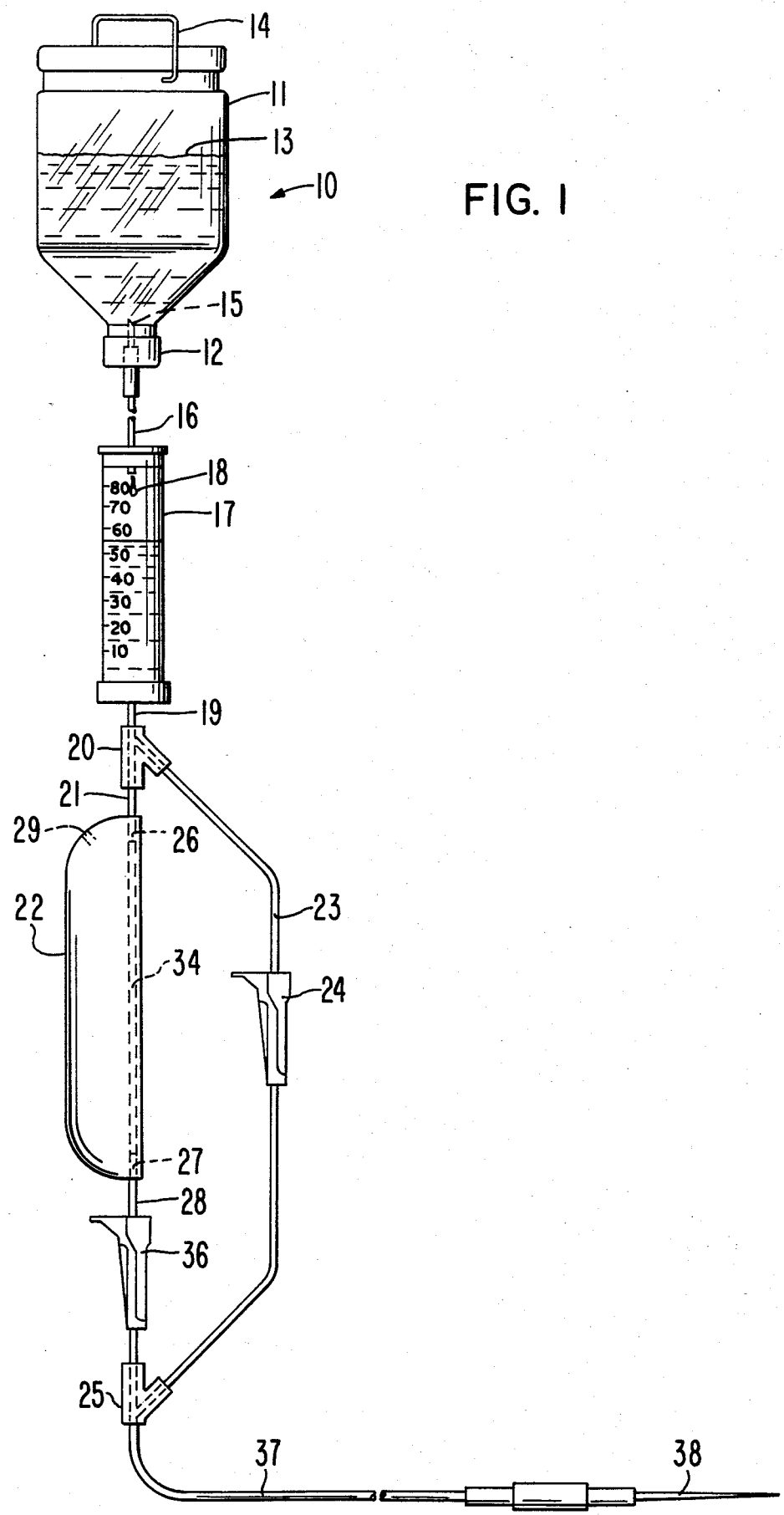
FIG. 1 is a perspective view of the parenteral delivery system provided by the invention comprising a flexible formulation container.

The accompanying drawing figures are not drawn to scale but they are set forth to illustrate various embodiments of the inventions. In the drawing figures and in the specification, like parts in related drawing figures are identified by like numbers. The terms appearing earlier in the specification are described hereinafter.

DETAILED DESCRIPTION OF THE DRAWINGS

FIG. 1 represents a parenteral delivery system provided by the invention and designated by the numeral 10. Delivery system 10 of FIG. 1 comprises a reservoir 11 suitably sealed or capped at 12, and it contains a medical fluid 13 acceptable for parenteral administration including intravenous administration. Reservoir 13 in the embodiment illustrated in FIG. 1 is a container made of glass. In another operative embodiment, reservoir 11 is a container formed of a flexible, or a semi-rigid, preferably transparent material designed as a parenteral bag 11. Transparent bag 11 can be made from a non-toxic plastic such as polyolefin, polyvinyl chloride, and the like. Reservoir 11 is supported in delivery position by support 14, and at its capped 12 end, reservoir 11 is connected to the rest of delivery system 10 through spike 15. Spike 15 is hollow and it pierces capped 12 end. The other end of spike 15 is connected to a section of medical grade tubing 16 that enters drip chamber 17. Spike 15 conveys medical fluid 13 dropwise 18 from reservoir 11 into drip chamber 17.

Medical fluid 13 is typically a sterile solution, such as a solution of dextrose, a solution of an electrolyte, or saline. Medical fluid 13 also is a pharmaceutical vehicle or carrier for parenteral administration, and it is a pharmaceutically acceptable carrier for a beneficial agent that is to be administered to a recipient. Drip chamber 17 is transparent and it is made of clear glass or plastic. Drip chamber 17 is used to trap air and it is used, in cooperation with a regulatory clamp, for adjusting the rate of flow of medical fluid 13 from reservoir 11 as the flow proceeds dropwise 18 through system 10.

Drip chamber 17 is connected through a section of medical tube 19 to one of the three tube-receiving ports of Y-type coupling member 20. Coupling member 20 is connected also through a section of medical tube 21 to a formulation chamber 22. A fluid by-pass 23 is provided and it is formed of a section of medical tube connected to coupling 25 for letting fluid 13 flow by formulation container 22. Tube by-pass 23 is provided with and it passes through regulator clamp 24, then it connects to a second Y-type coupling member 25 thereby letting fluid 13 flow directly through system 10 without flowing through formulation container 22.

Figure 2:
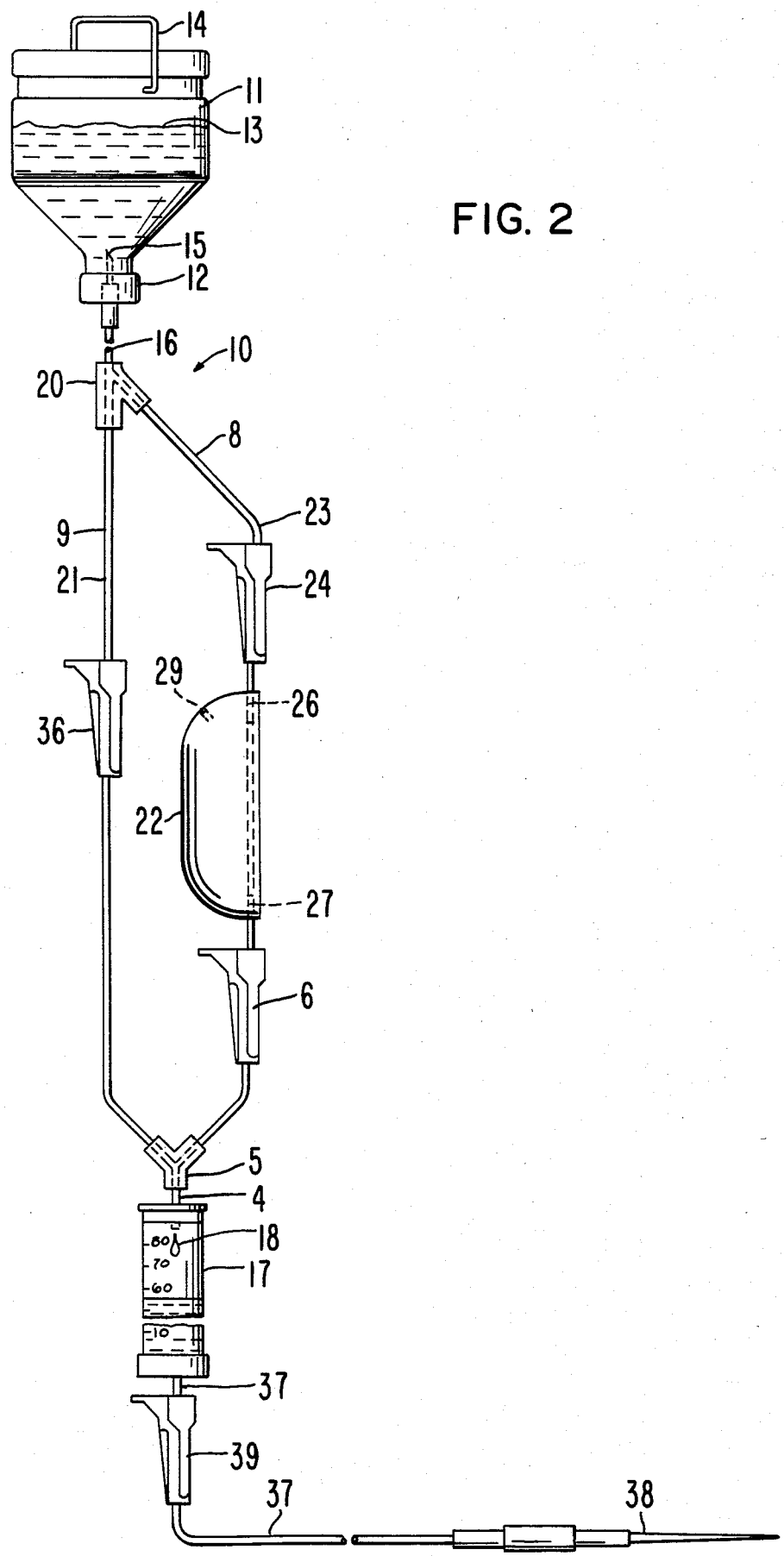
FIG. 2 is a perspective view of another embodiment of a parenteral delivery system provided by the invention comprising a flexible formulation container in a parallel path.

Formulation container 22, as seen in FIG. 1 and in FIG. 2, is sized and structure for use in parenteral delivery system 10. Formulation container 22 is self-contained, self-priming, self-powered and amenable to low cost manufacture. Formulation container 22 is lightweight and disposable, and it is provided with a receiving inlet 26 for receiving incoming tube 21 and it is provided with an outlet 27 for receiving outgoing tube 28. Tube 28 passes through a flow regulator 36 and into a coupling 25. A section of tubing 37 is connected to a skin-piercing means 38 for administration of fluid or agent formulation to a recipient. Formulation container 22 is made of plastic, preferably of a transparent plastic for viewing its internal contents, and it is optionally equipped with an air vent 29. In a presently preferred embodiment formulation chamber 22 is made of a flexible collapsible plastic nontoxic material.

FIG. 2 represents another parenteral delivery system 10 provided by the invention. In FIG. 2, delivery system 10 comprises a primary path 9 and a parallel path 8. Primary path 9 comprises a reservoir 11 suitably capped 12 for serving as a container for medical intravenously administrable fluid 13. Reservoir 11 is supported by support 14 and it is connected to the rest of delivery system 10 through spike 15. The other end of hollow spike 15 connects to tube 16 that enters coupling means 20. Primary path 9 is provided for the flow of medical fluid 13 essentially-free of added agent to a recipient. Primary path 9 comprises tube 21 that passes through flow regulator 36 and into Y-site 5. The Y-site 5 is in fluid communication through tube 4 with drip chamber 17. Drip chamber 17 is connected through tube 37, that passes through flow regulator 39 to skin-piercing means 38.

Parallel path 8 comprises tube 23 that is in fluid communication with primary path 9 and container 11 through coupling means 20. Tube 23 passes through a flow regulator clamp 24 into receiving port 26 of formulation container 22. Formulation container 22 is preferably provided with an air vent 29 for permitting trapped air to escape from system 10. Container 22 is provided with an outlet port 27 for receiving tube 7. Tube 7 passes through flow clamp 6 and into Y-coupling 5. The Y-coupling 5 is in fluid communication with drip chamber 17. Drip chamber 17 is connected through tube 37 that passes through regulator 39 to a skin-piercing member 38. The parallel flow path 8 provides a means for administering a fluid agent including drug formulation to a recipient. The primary 9, and parallel 8 of delivery system 10 of FIG. 2 further provides a means of diluting a fluid drug formulation by diluting it with fluid from primary path 9 at Y-site 5. Thus, the invention provides (a) continuous fluid administration, (b) continuous drug administration, (c) alternating fluid administration and drug administration, and (d) mixing and diluting of fluid and drug administration.

Figure 3:
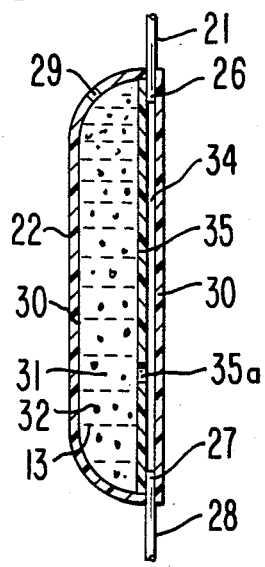
FIG. 3 is an opened view of the flexible container of FIGS. 1 and 2 illustrating the structure and the internal contents of the formulation container positioned in the parenteral delivery system.

FIG. 3 depicts formulation container 22 in opened section. In FIG. 3, formulation container 22 comprises a wall 30 and a wall 35 that surround and define an internal lumen 31. Lumen 31 contains a beneficial agent 32, and when delivery system 10 is in operation, it contains parenteral fluid 13. Wall 30 is formed of a nontoxic composition substantially impermeable to the passage of beneficial agent 32 and substantially impermeable to the passage of parenteral fluid 13. A passageway 34 extends through formulation container 22. Passageway 34 is formed by wall 35 postioned inside container 22. Wall 35 is formed of a composition, such as a polymer, permeable to the passage of beneficial agent 32, and it is permeable to the passage of parenteral fluid 13. Wall 35 and wall 30 are suitably united at contacting ends of formulation container 22 to form tube-like passageway 34. Passageway 34 extends through formulation container 22 and at inlet 26 it is FIG. 1 incoming tube 21, or in FIG. 2 incoming tube 23. Passageway 34 at its outlet receives, as in FIG. 1 tube 28, and as in FIG. 2 it receives tube 7. Passageway 34 receives the incoming tubes 21 and 23, and in either instance, incoming fluid 13 that passes through permeable wall 35 into lumen 31, wherein it forms a beneficial agent formulation 32 or solution. The latter solution passes out of lumen 31 through collapsible wall 35 and it reenters passageway 34. Alternatively, wall 35 can be formed of a semipermeable material with a passageway 35 or therethrough.

The formulation solution 32 in FIG. 1 leaves formulation container 22 through tube 28. The formulation solution 32 in FIG. 2 leaves formulation container 22 through tube 7. Further in FIG. 1, tube 28 passes through a flow regulator 36 and into coupling 25. The positioning of flow control clamp 36 insures that the hydrostatic fluid head provided by the fluid 13 level in reservoir 11 of FIG. 1 urges flexible wall 35 to collapse against wall 30 that is vented by vent 29. This hydrodynamic fluid collapsible combined operation thereby insures that essentially all of drug 32 will leave formulation chamber 22. A section of tubing 37 conveys fluid formulation solution 32 from coupling 25 to a skin-piercing means 38 for the administration of beneficial formulation agent solution 32, or alternatively fluid 13 to a recipient. Further in FIG. 2, tube 7 passes through clamp 6 to coupling means 5. A section of tubing 4 connects coupling 5 to drip chamber 17. Formulation solution 32 enters drip chamber 17 and leaves drip chamber 17 through tube 37. Tube 37 passes through clamp 39 and connects with skin-piercing means 38. Formulation chamber 22 in FIG. 1 operated in one preferred embodiment like the hydrodynamic collapsible operation as disclosed for FIG. 1. Alternatively, fluid 13 can enter drip chamber 17 and leave through tube 37. Thus, the invention in both operations provides and makes available continuous or interrupted administration, and intervals of agent-free administration.

Figure 4:
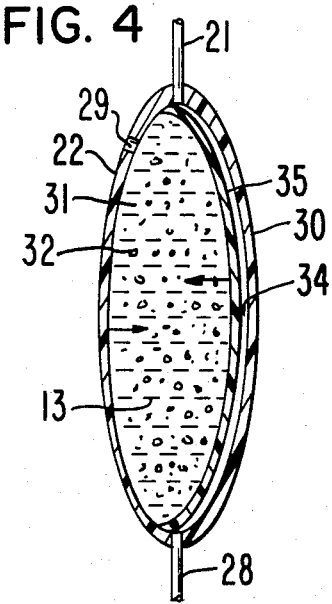
FIG. 4 is an opened view of another flexible container provided with a collapsible wall for use in a delivery system as illustrated in FIGS. 1 and 2.

FIG. 4 depicts formulation chamber 22 that embraces another configuration provided by the invention. In FIG. 4, wall 35 is made with a collapsible flexible polymer as it can collapse in the direction of the arrow, thereby effecting total delivery of drug from the chamber. In an optional embodiment wall 30 can be formed of a collapsible, flexible plastic, such as plasticize styrenebutadiene copolymer and it can collapse in the direction indicated by the arrow. The collapse of the wall insures essentially total delivery of all the drug.

Figure 5:
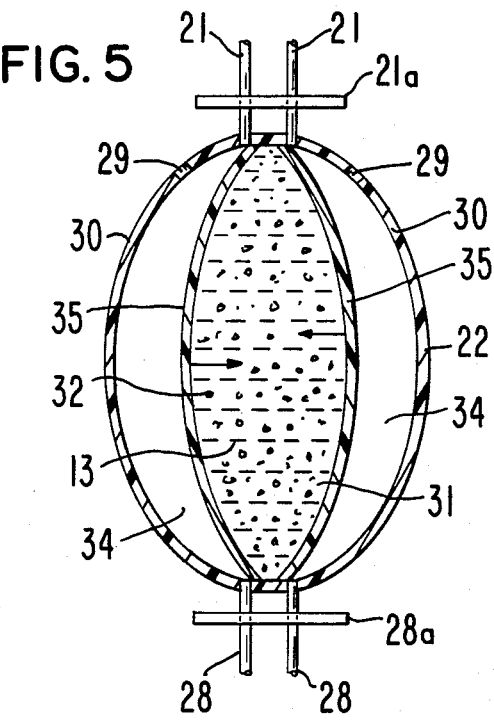
FIG. 5 is an opened view in cross-section of another flexible container with collapsible walls for use with the delivery system illustrated in FIGS. 1 and 2.

FIG. 5 depicts another formulation chamber provided by the invention. FIG. 5 depicts a container with an internal formulation chamber. The container comprises wall 30 and it is suitably equipped with air vent 29. A pair of inlet ports 21 lets fluid into passageway 34 that surrounds the inner formulation chamber. A pair of outlet ports 28 lets drug solution and fluid leave passageway 34. A three-way flow regulator 21a is provided to control the flow of fluid through port 21. The regulator can let fluid flow through both ports or through either port independently. A flow regulator 28a is provided on outlet ports 28. Regulator 28a is a three-way regulator and it permits flow through both outlet ports 28 simultaneously, or through either outlet independently. Wall 30 is formed of a fluid and agent impermeable polymer composition, and collapsible, flexible wall 35 formed of a semipermeable polymeric composition, or of a microporous polymeric composition. The formulation chamber operates as previously described.

The beneficial agent 32 in formulation container 22 can be in any pharmaceutical state that forms an agent formulation with a parenteral or medically acceptable fluid that enters formulation container 22. The use of formulation container 22 with agent 32 therein does not require any reconstituting, or admixture prior to use. Exemplary pharmaceutically acceptable forms that can be used in formulation container 22 include solid, crystalline, microcrystalline, particle, pellet, granules, powder, tablet, dry, spray-dried, lypophilized, forms that dissolve or undergo disintegration, or dissolution in the presence of a parenteral fluid, including intravenous fluid. The beneficial agent can be in a compressed form that undergoes distintegration and dissolution in the presence of a fluid such as compressed powders, compressed granules, in the form of friable layers of agent, and/or the like. Agent formulation container 22 generally will store an amount of agent for executing a prescribed therapeutic or beneficial program. That is, an amount of agent for the preprogrammed delivery of a therapeutically or a beneficially effective amount of agent to produce a therapeutic or a beneficial result. Agent formulation container 22 generally will have a capacity of from about 10 millimeters to 550 millimeters, or more, and it can house from 1 milligram to 150 grams of agent, or more.

Figure 6:
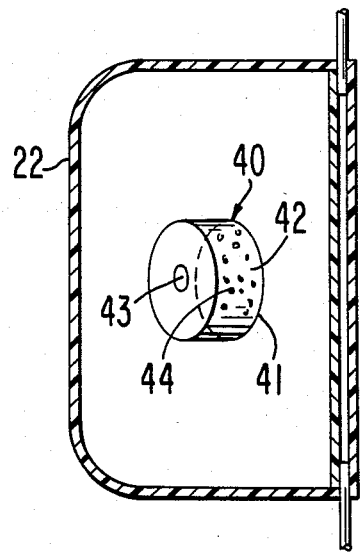
FIG. 6 is an opened view of a formulation container housing a means for delivering a drug which means is manufactured as an osmotic delivery device.

The beneficial agent in formulation container 22 can be present in a delivery device that releases the agent to fluid that enters container 22 and contacts the delivery device. Examples of delivery devices include, in one embodiment, the osmotic drug delivery device illustrated in FIG. 6. The osmotic device 40, seen in opened section, comprises a semipermeable wall 41 formed of a cellulose acylate, cellulose diacylate, cellulose triacylate, cellulose acetate, cellulose diacetate or cellulose triacetate, that surrounds and forms compartment 42 with the exterior of device 40. Compartment 42 contains a drug formulation 44, represented by dots, which drug formulation exhibits an osmotic pressure gradient across semipermeable wall 41 that enters flexible collapsible bag 22. The drug formulation can comprise a drug that exhibits an osmotic pressure gradient, or the drug formulation can comprise a drug mixed with an osmotically effective solute, such as sodium chloride, potassium chloride and the like, that exhibit an osmotic pressure substantially greater than the fluid in the flexible container 22. In operation, fluid that enters in the container is imbibed through the semipermeable wall of the device into the compartment in a tendency towards osmotic equilibrium at a rate determined by the permeability of the wall and the osmotic gradient across the wall thereby producing a solution that is dispensed through the passageway at a rate controlled by the device over a prolonged period of time. The delivery of drug formulation for homogenously blending with fluid in container 22, is controlled by device 40, and its rate of delivery is independent of the rate of fluid flow from the device, and the pH of the fluid in the chamber. Device 40 maintains its physical and chemical integrity throughout its releasing history. Drug delivery device 40, in the illustrated embodiment is an osmotic, rate-controlled solid drug dosage form as described by patentee Felix Theeuwes in U.S. Pat. No. 3,845,770.

Figure 7:
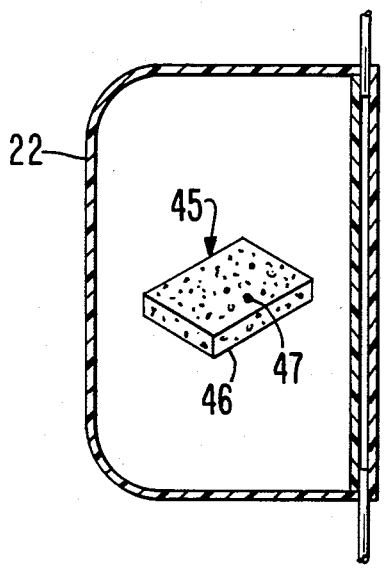
FIG. 7 is a view of a formulation container in opened view containing a drug delivery device comprising a matrix containing a drug.

FIG. 7 is a view of formulation container 22 having part of its housing removed and housing device 45 for delivering a drug into a medical fluid that enters container 22 for forming in situ an intravenously acceptable drug formulation solution. Device 45 comprise a matrix 46 containing drug 47 distributed therethrough. Matrix 47 is formed from a polymeric material that is non-erodible, that is, it keeps its physical and chemical integrity over time, and it is permeable to the passage of drug 47 by the process of diffusion. The rate of drug release from the matrix is determined by the rate the drug dissolves in and passes through the matrix by diffusion, so that from the matrix it is the drug release rate controlling step. The matrix can possess any shape such as rod, disc and the like that fits into container 22. The polymers include polyolefins such as polyethylene containing muscle relaxants and the like. Materials useful for manufacturing the devices are disclosed in U.S. Pat. No. 3,921,636.

Figure 8:
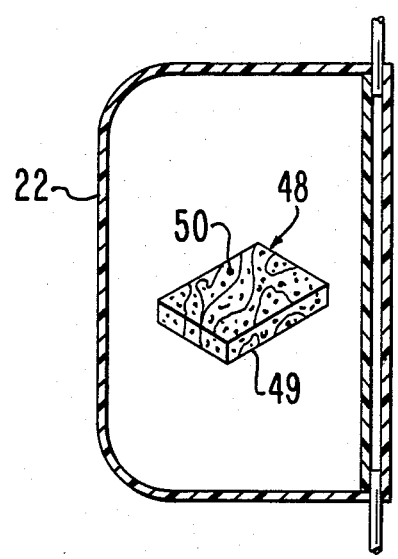
FIG. 8 is an opened view of a formulation container housing a drug delivery device comprising a microporous matrix containing drug.

FIG. 8 is a view of drug formulation container 22, in opened view, housing device 48 for delivering a drug into a fluid that enters container 22. Device 48 is seen in opened section, and it is formed of a microporous polymeric material 49 containing drug 50 distributed therethrough. Matrix 49 is formed of a non-toxic, inert polymer, that is non-erodible and has a plurality of micropores for releasing drug at a controlled rate to fluid entering container 22. Microporous materials useful for the present purpose are disclosed in U.S. Pat. Nos. 3,797,494 and 3,948,254.

Figure 9:
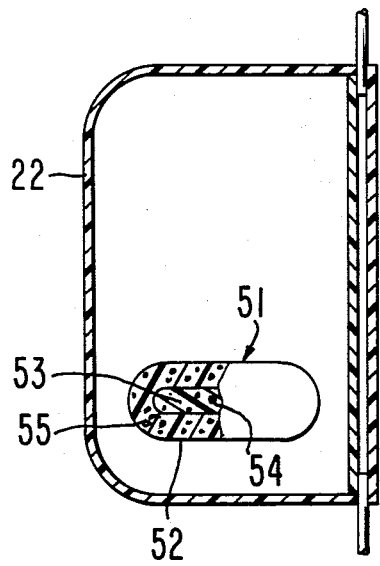
FIG. 9 is an opened view of a formulation container housing a drug delivery device comprising a microporous membrane surrounding a reservoir containing drug.

FIG. 9 illustrates drug formulation container 22, with a part of its wall removed, housing another device 51 for delivering a drug into a liquid that enters container 22 form forming an intravenously acceptable drug formulation. Device 51 is seen in opened-section and it comprises a wall 52 surrounding a reservoir 53 containing a drug 54. The reservoir is formed of a solid carrier permeable to the passage of drug such as cured polydimethylsiloxane containing diazepam. Wall 52 is formed of a microporous material, the pores 55 of which contain a drug release rate controlling medium permeable to the passage of drug 54, for example, formed of a microporous polymer made by coprecipitation of a polycation and a polyanion. The release of drug 54 is controlled by device 51, which device maintains its physical and chemical integrity during the period of time it is in container 22. Device 51 is disclosed in U.S. Pat. No. 3,993,072, which patent is incorporated herein by reference.

Figure 10:
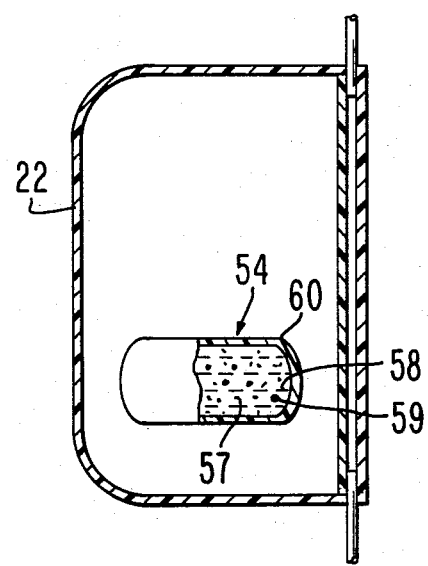
FIG. 10 is an opened view of a formulation container having a drug delivery device comprising a rate controlling membrane surrounding a liquid reservoir containing drug.

FIG. 10 illustrates drug formulation container 22, with a section of its wall removed, housing delivery device 56 for delivering a drug at a rate controlled by device 56 into a fluid that enters container 22. Device 56 is seen in opened-section and it comprises a reservoir 57 formed of a liquid mass transfer conductor 58 such as a medical oil liquid carrier, permeable to the passage of drug, containing drug 59 such as phenobarbital. Reservoir 57 is surrounded by a wall 60 formed of a drug release rate controlling material permeable to the passage of drug 59, such as a polyolefin. The rate of passage of drug 59 is lower than the rate of passage through conductor 58, so that drug release by wall 59 is the drug release rate controlling step for releasing drug 59 from device 56. Device 56 maintains its physical and chemical integrity throughout its drug release history. Drug delivery device 56 is disclosed in U.S. Pat. No. 3,993,073, which patent is incorporated herein.

Figure 11:
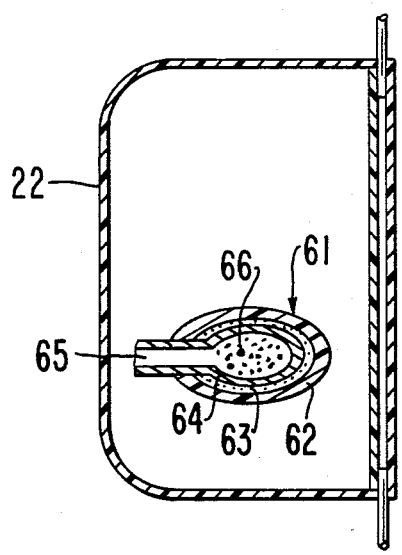
FIG. 11 is a view of a drug formulation container housing a drug deliver comprising a housing and driving member surrounding a flexible container.

FIG. 11 illustrates drug formulation container 22, in opened view, containing device 61 useful for delivering a drug into a medically acceptable fluid passing through container 22. Device 61 is seen in opened view and it comprises an exterior wall 62 formed of a semipermeable polymer permeable to fluid and substantially impermeable to the passage of drugs and solutes. A layer 63 of an osmotically effective solute, for example sodium chloride, is deposited on the inner surface of wall 62. Solute 63 surrounds an inner container 64 formed of a flexible material that is impermeable to solute and drug. Container 64 has a passageway 65 for delivering a drug 66 into a fluid in container 22. Device 61 dispenses drug by fluid permeating from container 22 through the outer wall 62 to continuously dissolve solute 63 in a tendency towards osmotic equilibrium, thereby continuously increasing the volume between wall 62 and container 64. This increase causes container 64 to continuously collapse and dispense drug 66 from device 61 at a controlled rate through passageway 65 to fluid passing through container 72. Osmotically powered agent dispensing devices are disclosed in U.S. Pat. Nos. 3,760,984 and 3,995,631.

Figure 12:
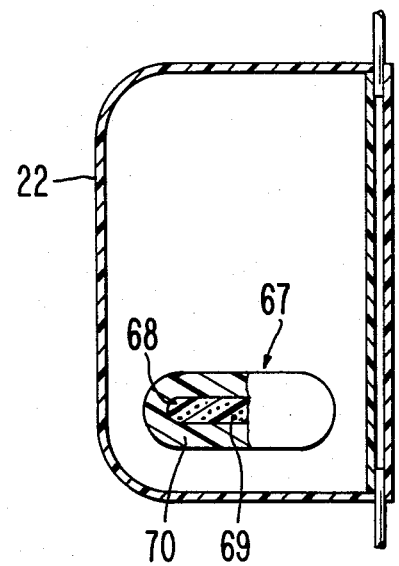
FIG. 12 is a view of a drug formulation container housing a drug delivery device comprising a drug release rate controlling membrane surrounding a solid reservoir containing drug.

FIG. 12 depicts drug formulation container 22, in opened section, containing another device 67 for delivering a drug into an intravenously acceptable fluid that enters container 22. Device 67 is illustrated in opened-section and it comprises an inner mass transfer conductor 68, illustrated as a solid core and formed of a polymeric material such as cured polydimethylisoxane, with drug 69 dispersed therethrough. Surrounding mass transfer conductor 68 is a drug release rate controlling membrane 70, preferrably formed of a polymeric material, such as polyethylene. Both conductor 68 and membrane 70 are permeable to the passage of drug 69 by diffusion, that is, drug can dissolve in and diffuse through conductor 68 and membrane 70. However, the permeability of conductor 68 is greater than that of membrane 70, and membrane 70 thus acts as the rate controlling member for drug release from device 67. Device 67 maintains its physical and chemical integrity throughout the period of drug delivery. Drug delivery device 67 is disclosed in U.S. Pat. No. 3,845,480.

Figure 13:
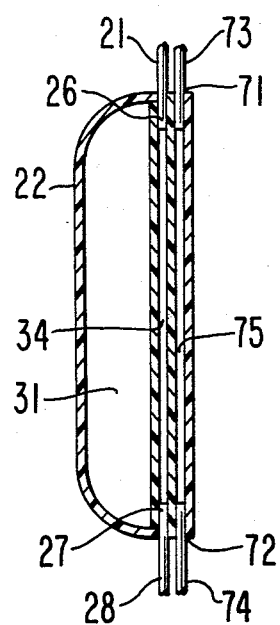
FIG. 13 is an opened view of a formulation container provided with twin passageways.

FIG. 13 depicts, in opened section, another embodiment, of formulation, flexible container 22. Container 22 of FIG. 13 is an embodiment of container 22 of FIG. 3. Container 22, as previously noted is made of a flexible, collapsible polymeric wall forming composition. Container 22 is provided with an additional inlet 71 and with an additional outlet 72 for receiving incoming tube 73 and outgoing tube 74. In FIG. 13, container 22 has an additional passageway 75 that extends through container 22. Passageway 75 is free of direct contact with the lumen 31 of container 22. Passageway 75 provides another means for passing medical fluid through the intravenous system without adding a beneficial agent to the fluid. Thus, passageway 75 provides for the administration of a medical fluid that is free of beneficial agent.

Figure 14:
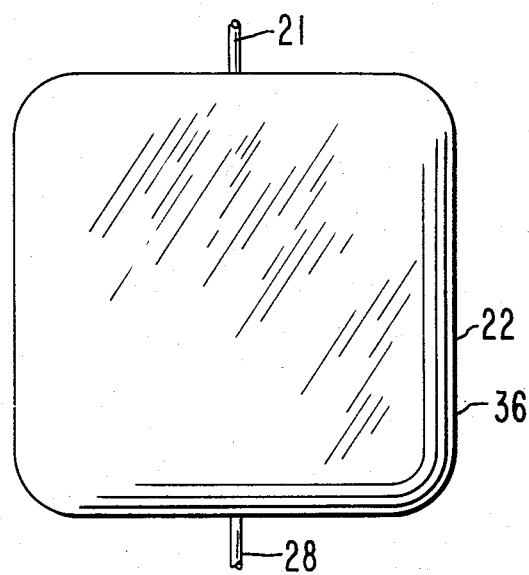
FIG. 14 is a front view of the flexible container of FIGS. 1 and 2.

FIG. 14 and FIG. 15 depict formulation container 22 as seen in different views. FIG. 14 depicts a front view of formulation container 22. FIG. 15 depicts a back view of formulation container 22 as seen in opened section at 4. Container 22 is flexible or semi-rigid and it comprises a first wall 3 and a second wall 2 with a section of the latter wall removed at 4 for illustrating the first wall. Wall 3 and wall 2 are joined around their periphery to form and define internal lumen or space 31. Wall 2 and wall 3 are made of fluid and agent impermeable materials. A third internal wall 35, not seen in FIGS. 14 and 15, but seen in FIG. 13, is sealed in a small area of lumen 31 to define one wall of passageway 34. As seen in FIG. 15, lumen 31 contains fluid 13 and beneficial agent 32. FIG. 16 depicts an expanded view of incoming tube 21 entering inlet 26 and outgoing tube 28 in contact with outlet 27.

The expression beneficial agent, as used herein, generically denotes any substance that produces a therapeutic or a beneficial result, such as a drug, a carbohydrate, an electrolyte and/or the like. The term fluid or liquid denotes a fluid or a liquid that can be administered parenterally including intravenously, comprising pharmaceutically acceptable fluids that are also pharmaceutically acceptable carriers for an agent. Exemplary fluids include isotonic saline, Ringer's lactate, and the like. The term formulation, and agent formulation as presently used herein, generically indicates the beneficial agent is formulated, mixed, added, dissolved, suspended, solubilized, formulated into a solution, carried and/or the like in or by the fluid in a physical-chemical form acceptable for parenteral including intravenous administration. The expression beneficial agent is used for agent in the container in pharmaceutical form and for agent in a delivery device.

The materials suitable for forming the wall generally are clear, able to withstand autoclaving at 240° F. to 270° F., are suitable for film-forming and/or extrusion, are soft to handle, and they should not hydrolyze and or leach into parenteral fluids. Representative substantially impermeable materials suitable for the present purpose include polyvinyl chloride that heat seals between 275° and 350° F.; dense polyethylene that heat seals between 260° and 375° F.; Mylar ® polyester that heat seals between 325° and 450° F.; polycarbonate that heat seals between 330° and 440° F.; fluorinated ethylene that heat seals between 575° and 700° F.; polyvinyl fluoride that heat seals between 400° and 425° F., polytriflurochloroethylene that heat seals between 325° and 375° F.; permeable ethylene-vinyl acetate that heat seals between 250° and 350° F.; and the like. In an embodiment, the peripheries can be joined by adhesive sealing using an adhesive stable in the presence of fluids.

In operation, formulation container 22 formed of the nontoxic, flexible material receives incoming fluid that contacts with (a) agent in the formulation container 22 to form a fluid agent formulation, or (b) contacts a delivery device for forming a fluid agent formulation with agent released from the delivery device. In both operations, (a) or (b), the formulation container collapses continuously, or at the end of the delivery period. This action assures complete delivery of the beneficial agent to a recipient.

This novel invention uses means for the obtainment of precise control of drug release into an intravenous therapeutic system. While there has been described and pointed out features of the invention as applied to presently preferred embodiments, those skilled in the art will appreciate that various modifications, changes, additions, and omissions in the system illustrated and described can be made without departing from the spirit of the invention.

We claim:

1. A method for the administration of a beneficial drug to an animal, which method comprises:
   (a) admitting into the animal a delivery member in fluid communication with an intravenous delivery system, the system comprising:
      (1) a reservoir of a pharmaceutically acceptable fluid;
      (2) a drip chamber in fluid communication with the reservoir;
      (3) a container in fluid communication with the drip chamber and with the delivery member, the container comprising:
         (i) a wall that surrounds a lumen, said wall formed of a flexible material that moves from an expanded position to a collapsed position as drug formulation leaves the container;
         (ii) a passageway through the container, said passageway formed of a material that permits a fluid to enter the container and permits a fluid drug formulation to leave the container;
         (iii) a beneficial drug in the container that forms a fluid drug formulation with fluid that enters the container; and,
   (b) administering the drug to the animal by letting fluid enter the container to form the fluid drug formulation that, as the container collapses, leaves the container for administering to the animal.

2. A parenteral delivery system for administering a beneficial drug to a recipient, the delivery system comprising;
   (a) a reservoir of a pharmaceutically acceptable fluid;
   (b) a drip chamber in fluid communication with the reservoir; and,
   (c) a container in fluid communication with the drip chamber, the container comprising:
      (1) a wall that surrounds a lumen, said wall formed of a flexible, fluid and agent impervious material capable of changing from a expanded to a collapsed position over time;
      (2) a passageway in the wall and extended through the lumen for letting fluid enter the lumen, and for letting a fluid drug formulation leave the lumen, the passageway formed of a material that permits the passage of fluid and fluid drug formulation over time; and,
      (3) a beneficial drug in the lumen that forms a fluid drug formulation with fluid that enters the container.

3. The parenteral delivery system for administering the beneficial drug according to claim 2, wherein the drug in the lumen is in a solid pharmaceutically acceptable dosage form.

4. The parenteral delivery system for administering the beneficial drug according to claim 2, wherein the drug in the lumen is in a delivery device that releases the drug to fluid that enters the lumen.

5. The parenteral delivery system for administering the beneficial drug according to claim 2, wherein an additional passageway extends through the lumen, said additional passageway formed of a material impervious to the passage of fluid and fluid drug formulation.

6. The parenteral delivery system for the administering the beneficial drug according to claim 2, wherein the delivery system comprises a fluid flow path that circumscribes the container.

7. A method for administering a beneficial agent to an animal, which method comprises:
   (a) admitting into the animal a delivery member in fluid communication with an intravenous delivery system, the system comprising:
      (1) a reservoir of a pharmaceutically acceptable fluid;
      (2) a drip chamber in direct fluid communication with the reservoir and with the delivery member; and,
      (3) a fluid path that circumvents the direct path, said fluid path comprising:
         (i) a container in fluid communication with the reservoir and in fluid communication with the drip chamber, the container comprising:
            (a) a wall that surrounds an internal lumen, said wall formed of a flexible material that collapses as a drug formulation leaves the container;
            (b) a passageway through the lumen, said passageway form of a material that permits a fluid to enter the lumen and permits a fluid drug formulation to leave the lumen;
            (c) a beneficial drug in the lumen that forms a fluid drug formulation with fluid that enters the lumen; and,
   (b) administering the drug to the animal by letting fluid enter the container to form the fluid drug formulation, that as the container collapses, leaves the container and passes through the drip chamber for administering to the animal.

8. A parenteral delivery system for administering a beneficial drug to a recipient, the delivery system comprising:
   (a) a reservoir of a pharmaceutically acceptable fluid;
   (b) a drip chamber in direct fluid communication with the reservoir; and,
   (c) a fluid path that circumvents the direct path, said circumventing fluid path comprising:
      (i) a container in fluid communication with the reservoir and in fluid communication with the drip chamber; said container comprising:
         (a) a wall that surrounds an internal lumen, said wall formed of a flexible material that collapses as a drug formulation leaves the container;
         (b) a passageway through the lumen for letting fluid enter the lumen and for letting fluid drug formulation leave the lumen, said passageway formed of a material that permits the passage of fluid into the lumen and permits the passage of drug formulation from the lumen; and,
         (c) a beneficial drug in the lumen that forms a fluid drug formulation with fluid that enter the lumen.

9. The parenteral delivery system for administering the beneficial drug according to claim 8, wherein the drug in the lumen is in a solid pharmaceutically acceptable form.

10. The parenteral delivery system for administering the beneficial drug according to claim 8, wherein the drug in the lumen is in a delivery device that releases the drug to fluid that enters the lumen.

11. The parenteral delivery system for administering the beneficial drug according to claim 8, wherein an additional passageway extends through the lumen, said additional passageway formed of a material impermeable to the passage of fluid and impermeable to the passage of drug formulation.

12. The parenteral delivery system for administering the beneficial drug according to claim 8, wherein the delivery system comprises a flow regulator clamp.

* * * * *